United States Patent [19]

Ichishima et al.

[11] Patent Number: 4,480,037
[45] Date of Patent: Oct. 30, 1984

[54] ALKALINE PROTEASE AND PREPARATION METHOD THEREOF

[75] Inventors: Fiji Ichishima, Fuchu; Takashi Onouchi, Tokyo, both of Japan

[73] Assignee: Showa Denko Kabushiki Kaisha, Tokyo, Japan

[21] Appl. No.: 465,064

[22] Filed: Feb. 8, 1983

[30] Foreign Application Priority Data

Feb. 8, 1982 [JP] Japan ................................ 57-17596

[51] Int. Cl.$^3$ .................. C12N 9/54; C12N 9/56; C12R 1/07
[52] U.S. Cl. ................................ 435/221; 435/222; 435/832; 252/DIG. 12
[58] Field of Search ................................ 435/221, 220

[56] References Cited

U.S. PATENT DOCUMENTS

| | | | |
|---|---|---|---|
| 3,827,938 | 8/1974 | Aunstrup et al. | 435/221 |
| 3,871,963 | 3/1975 | Tobe et al. | 435/221 |
| 3,905,869 | 9/1975 | Hidaka et al. | 435/221 |
| 4,002,572 | 1/1977 | te Nijenhuis | 435/221 X |
| 4,052,262 | 10/1977 | Horikoshi et al. | 435/221 |

FOREIGN PATENT DOCUMENTS 1263765  2/1972  United Kingdom .

*Primary Examiner*—Lionel M. Shapiro

*Attorney, Agent, or Firm*—Sughrue, Mion, Zinn, Macpeak & Seas

[57] ABSTRACT

Alkaline protease API-21 having the following physicochemical properties:

(1) Activity: Hydrolyzes casein under alkaline conditions, optimum pH range is 10 to 11, and has optimum temperature range for activity of 45° C. to 50° C.;

(2) Stability: No decrease in enzymatic activity observed up to 40° C. upon heating without substrated for 10 minutes at a pH of 10, but 90% or more decrease of enzymatic activity observed at 50° C. for 10 minutes at a pH of 10. Deactivation occurs at 50° C. for 10 minutes at a pH of 8 and complete deactivation substantially occurs at 60° C. for 10 minutes at a pH of 8. The protease is stable under alkaline conditions, especially within a pH range of 7 to 11.5, and is stable against freezing and freeze-drying; and (3) Enzyme molecule: The protease is protein having a molecular weight of about 22000 as estimated by a gel filtration method, an isoelectric point of 7.4 as estimated by an electrofocusing method, an absorption peak of 275 to 282 nm in a UV absorption spectrum, IR absorption characteristics as shown in FIG. 5, and a serine residue is the active site thereof.

This alkaline protease is prepared by cultivating novel species of NKS-21 belonging to genus Bacillus.

2 Claims, 6 Drawing Figures

ALKALINE PROTEASE AND PREPARATION METHOD THEREOF

BACKGROUND OF THE INVENTION

1. Field of the Invention

The present invention relates to novel alkaline protease API-21 and the preparation method thereof. More specifically, it relates to alkaline protease API-21 derived from a bacterium and having an enzymatic activity even at a relatively low temperature (e.g., room temperature to about 40° C.) under an alkaline condition and also relates to a method for preparing the same from the cultivation of novel species of NKS-21 belonging to genus Bacillus.

2. Description of the Prior Art

Alkaline protease is widely used in the fields of, for example, a leather industry, a food industry, a fiber or textile industry, or a medicine or pharmaceutical industry; the reason is said to be that alkaline protease is rather stable against heat as compared with neutral protease. Furthermore, market demand for enzmes as a detergent additive has recently increased. Enzymes practically used as a detergent additive are alkaline proteases derived from bacteria belonging to genus Bacillus, which exhibit a maximum activity at a pH of about 9 to about 10. Most of the above-mentioned enzymes exhibit a maximum activity at a relatively high temperature, especially around 60° C., but are inactive or less active at a relatively low temperature, especially around a room temperature. This means that the characteristics of enzymes are not fully utilized in such a country as in Japan, where clothes are generally washed at room temperature. Furthermore, the development of enzymes having a retained enzymatic activity even at a relatively low temperature is needed due to the recent increased usage of chemical fiber clothes having a relatively low heat stability and also due to the recent energy-saving movement.

SUMMARY OF THE INVENTION

Accordingly, the objects of the present invention are to eliminate the above-mentioned disadvantages of known alkaline protease by providing a novel alkaline protease having a high enzymatic activity at a relatively low temperature.

Another object of the present invention is to provide a method for preparing a novel alkaline protease having a high enzymatic activity from a novel bacterium capable of producing the same.

Other objects and advantages of the present invention will be apparent from the following description.

Figure 5:
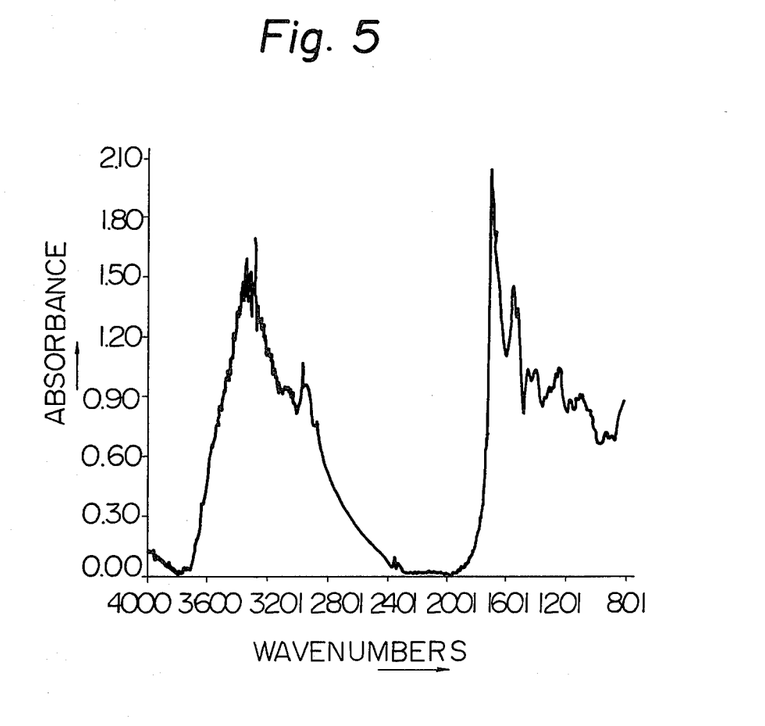
FIG. 5 illustrates the Fourier Transform Infrared Spectrum of the enzyme according to the present invention.

In accordance with the present invention, there is provided alkaline protease API-21 having the following physicochemical properties:

(1) Activity: Hydrolyzes casein under alkaline conditions, with an optimum pH range of 10 to 11, and has optimum temperature range for activity of 45° C. to 50° C.;

(2) Stability: No decrease in enzymatic activity observed up to 40° C. upon heating without substrate for 10 minutes at a pH of 10, but 90% or more decrease of enzymatic activity observed at 50° C. for 10 minutes at a pH of 10. Deactivation occurs at 50° C. for 10 minutes at a pH of 8 and complete deactivation substantially occurs at 60° C. for 10 minutes at a pH of 8. The protease is stable under alkaline conditions, especially within a pH range of 7 to 11.5, and is stable against freezing and freeze-drying; and (3) Enzyme molecule: The protease is protein having a molecular weight of about 22000 as estimated by a gel filtration over Sephadex G-75 (Trademark) at a pH of 10, an isoelectric point of 7.4 as estimated by an electrofocusing method, an absorption peak of 275 to 282 nm in a UV absorption spectrum, IR absorption characteristics as shown in FIG. 5, and a serine residue in the active site thereof.

In accordance with the present invention, there is also provided a method for preparing alkaline protease API-21 comprising the steps of:

(a) cultivating species of NKS-21 of genus Bacillus capable of producing alkaline protease API-21 in an alkaline culture medium; and (b) recovering alkaline protease API-21 from the cultured product.

BRIEF DESCRIPTION OF THE DRAWINGS

The present invention will be better understood from the description set forth below with reference to the accompanying drawings, in which.

DESCRIPTION OF THE PREFERRED EMBODIMENTS

The inventors studied the bacteria which can produce alkaline protease having a high activity at a relatively low temperature. As a result of the classification and search of numerous strains of bacteria isolated from natural soil, the novel bacterium belonging to genus *Bacillus sp. nov.* NKS-21 (referred to as NKS-21 hereinbelow) which can produce alkaline protease having a high activity at a relatively low temperature was isolated from the natural soils at Fuchu-shi, Tokyo, Japan. It has been found from the microbiological properties thereof that a strain NKS-21 capable of producing alkaline protease API-21 according to the present invention is a novel aerobic sporangium bacterium belonging to genus Bacillus.

This bacterium NKS-21 has been deposited since Feb. 3, 1982 in the Fermentation Research Institute (FRI) in Japan as Bacillus sp. FERM BP-93 under Budapest Treaty on the International Recognition of the Deposit of Microorganisms for the Purposes of Patent Procedure.

The microbiological properties of this bacterium are explained below. The reagents and isolation methods used for the determination of the microbiological properties of the bacterium NKS-21 were according to the description in "Bergey's Manual of Determinative Bacteriology" (8th edition) (1974). The isolation of the bacterium from soil was carried out as follows: That is, a small amount of a soil mass was added to a peptone medium and the cultivation was carried out by using a shaking cultivator under the conditions of a pH of 7 to 10 and a temperature of 10 to 40° C. for 40 to 150 hours. A portion of the cultured product was spread on agar plates and the strain was isolated by a usual pure isolation method.

MICROBIOLOGICAL PROPERTIES OF NKS-21

(a) Morphological Characteristics (1) Size of vegitative cells: 0.6-0.8 μm×2.5-3.5 μm (micrometer).
(2) Cell pleomorphism: Cells sometimes expand to a size of 0.6-1.0 μm×4.5 μm.
(3) Gram stain: Positive but easily decolorized.
(4) Motility: Motile with peritrichous flagella.
(5) Spores: Oval to elliptical, subterminal, 0.8 μm×1.2 μm.
(6) Sprangia: Slightly swollen.
(7) Acid resistance: Negative.

(b) Cultural Characteristics in Various Media (1) Peptone broth:
  (i) pH 9.5: Good growth both at 20° C. and 30° C., pH 7.2: Scant growth at 20° C. and good growth at 30° C.
  (ii) Growth temperature at a pH of 9.5, Growth between 14° C. and 41° C., No growth above 43° C. or below 12° C.
(2) Other media:
  Meat extract.peptone agar slant: Good growth,
  Meat extract.peptone broth containing 7% sodium chloride: Good growth,
  Meat extract.peptone broth: Good growth,
  Casein.meat extract.peptone agar slant: Good growth,
  Casein.meat extract.peptone broth: Good growth,
  Starch.peptone broth: Good growth,
  Glucose.peptone broth: Good growth,
  Tripton.yeast extract agar plate: Good growth,
  Starch.yeast extract broth: Growth,
  Meat extract.gelatine stab:
  (i) pH 10.0, 30° C., Growth and liquefaction.
  (ii) pH 10.0, 20° C., Weak surface growth and weak liquefaction.
  (iii) pH 7.2, 30° C., Growth and liquefaction.
  (iv) pH 7.2, 20° C., Weak surface growth and weak liquefaction.
(3) Growth in anaerobic conditions: No growth in anaerobic conditions, but growth in aerobic conditions.

(c) Physiological Characteristics (1) Reduction of nitrate to nitrite: no reduction.
(2) Anaerobic production of gas from nitrate: negative.
(3) Methyl red (MR) test: negative.
(4) Voges-Proskauer (VP) test: negative.
(5) Production of indole: none.
(6) Production of H$_2$S: none.
(7) Hydrolysis of starch: positive.
(8) Utilization of citrate: positive.
(9) Utilization of inorganic nitrogen source: utilize nitrates and ammonium salts.
(10) Production of pigment: none.
(11) Urease test: negative.
(12) Cytochrome oxidase test: positive.
(13) Catalase test: positive.
(14) O-F test (Hugh and Leifson's medium): weak fermentation.
(15) Acid production and gas generation from carbohydrates:

|  | acid production | gas generation |
| --- | --- | --- |
| L-Arabinose | − | − |
| D-Xylose | − | − |
| D-Glucose | + | − |
| D-Mannose | + | − |
| D-Fructose | − | − |
| D-Galactose | + | − |
| Maltose | + | − |
| Sucrose | + | − |
| Lactose | − | − |
| Trehalose | + | − |
| D-Sorbitol | + | − |
| D-Mannitol | + | − |
| Inositol | + | − |
| Glycerol | + | − |
| Starch | + | − |
| Ribose | − | − |
| Raffinose | + | − |
| Cellobiose | + | − |

(Remarks) +: positive, −: negative (16) Others
  (i) Deamination of phenylalanine: positive.
  (ii) Hydrolysis of casein: positive.
  (iii) Decomposition of tyrosine: positive.

As shown above, the strain NKS-21 according to the present invention is an aerobic sporangium bacterium, which is clearly believed to belong to the genus Bacillus. The characteristic features of this strain are that the strain grows in neutral to alkaline medium, and that the optimum pH range for growth is 8 to 10. These microbiological properties are similar to those of known strains *Bacillus pasteurii* and *Bacillus alcalophilus*. The strain NKS-21 according to the present invention, however, is clearly distinguished from the above-mentioned two strains in some microbiological properties, although some microbiological properties of the strain NKS-21 are the same as those of the above-mentioned known strains. For example, both the strains *Bacillus pasteurii* and *Bacillus alcalophilus* grow in an alkaline pH region but the latter can not grow at a pH of 7. Contrary to this, NKS-21 grows well in an alkaline pH region, but still grows well at a neutral pH. Accordingly, NKS-21 is different from *Bacillus alcalophilus* in this point. Furthermore, *Bacillus pasteurii* does not hydrolyze starch, but NKS-21 hydrolyzes starch. In addition, NKS-21 is distinguished from *Bacillus pasteurii* in the following points:

(1) *Bacillus pasteurii* reduces nitrates, whereas NKS-21 does not reduce nitrates;
(2) *Bacillus pasteurii* has endospores in the shape of a sphere or near oval, whereas the endospores of NKS-21 are oval to elliptical; and
(3) *Bacillus pasteurii* decomposes urea, whereas NKS-21 does not decompose urea.

From the above-mentioned differences in microbiological properties, NKS-21 is clearly different from *Bacillus pasteurii*.

The classification data of *Bacillus alcalophilus* is not described in detail in the above-mentioned "Bergey's Manual of Determinative Bacteriology". As the standard strain of *Bacillus alcalophilus* was not available, the microbiological properties of NKS-21 were experimentally compared with those of the original strains *Bacillus*

*alcalophilus* NCIB 10436 and NCIB 10438 cited in the "Bergey's Manual of Determinative Bacteriology". Both NCIB 10436 and NCIB 10438 were slight positive in Gram staining reaction and were easily decolorized. These properties are similar to those of NKS-21. Regarding the morphological characteristics of the vegitative cells, short rods having a size of 0.7 $\mu m \times 2.0$ $\mu m$ and long rods having a size of 0.8 $\mu m \times 4.6$ $\mu m$ were observed by an electron microscope in NCIB 10436, and vegetative cells having a size of 0.7 $\mu m \times 1.5$ $\mu m$ were observed in NCIB 10438. Contrary to this, the size of the vegitative cells of NKS-21 was 0.6–0.8 $\mu m \times 2.5$–3.5 $\mu m$ by an electron microscopic observation and the endospores thereof have an oval to elliptical shape having a size of 0.8 $\mu m \times 1.2$ $\mu m$. Motility in NCIB 10436 and 10438 was not observed, whereas NKS-21 is motile. Furthermore, the physiological properties of NKS-21 are clearly different from those of NCIB 10436 and NCIB 10438 in the following points:

(1) *Bacillus alcalophilus* NCIB 10436 and NCIB 10438 did not grow in a mannitol medium, whereas NKS-21 grew therein; and (2) NCIB 10436 did not grow in a meat extract peptone broth containing 7% sodium chloride, whereas NCIB 10438 and NKS-21 grew therein.

From the above-mentioned differences, NKS-21 is distinguished from *Bacillus alcalophilus* NCIB 10436 and NCIB 10438, although some microbiological properties of NKS-21 are similar to those of the *Bacillus alcalophilus*.

Furthermore, NKS-21 is similar to *Bacillus subtilis* in the points that the size of the vegitative cells of *Bacillus subtilis* is 0.7 to 0.8 $\mu m$ in width and 2 to 3 $\mu m$ in length and that *Bacillus subtilis* decomposes starch. However, NKS-21 is distinguished from *Bacillus subtilis* in the following points:

(1) *Bacillus subtilis* grows well at a pH of 5.5 to 8.5, but does not grow at a pH of 9 to 10, at which NKS-21 grows well; and (2) The maximum growth temperature of *Bacillus subtilis* is 45° C. to 55° C., whereas NKS-21 does not grow at above 43° C.

Accordingly, NKS-21 is clearly different from *Bacillus subtilis*.

Thus, NKS-21 is clearly distinguished in the microbiological properties from known *Bacillus pasteurii*, *Bacillus alcalophilus* and *Bacillus subtilis* and any strain having the same microbiological properties as NKS-21 is not described in the "Bergey's Manual of Determinative Bacteriology". Accordingly, NKS-21 is identified as a novel strain belonging to genus Bacillus.

According to the present invention, novel alkaline protease API-21 having a high activity at a relatively low temperature is prepared by cultivating the novel NKS-21 in an alkaline culture medium, followed by recovering from the cultured product. The microorganisms usable in the cultivation are not limited to NKS-21, but the microorganisms including natural or artificial mutants of NKS-21 can also be used as long as they can produce alkaline protease API-21. These microorganisms are included within the scope of the present invention.

The novel alkaline protease API-21 obtained from the cultivation of NKS-21 according to the present invention will now be explained in detail.

NKS-21 can be aerobically cultured, for example, in a peptone culture medium having a pH of 8 to 10 by a shaking culture or aerobic agitating culture after inoculation of NKS-21 into the culture medium at a temperature of 10°10 C. to 40° C. for 40 to 150 hours. After the completion of cultivation, the cultivated microbial cells are readily separated from the cultured product and the clear cultivation supernatant solution can be obtained. The alkaline protease API-21 is readily precipitated by the addition of an organic solvent such as ethanol to the supernatant solution. The precipitated alkaline protease API-21 is subjected to centrifugal separation and is freeze-dried in vacuo. Thus, the desired enzyme, alkaline protease API-21 can be obtained.

The activity of the alkaline API-21 thus obtained is determined as follows.

The cultivated clear solution or the enzyme solution is appropriately diluted with 0.1 M sodium carbonate—0.1 M boric acid—potassium chloride buffer solution (pH 10.0). To 0.5 ml of the resultant solution, 0.5 ml of 2% milk-casein solution having a pH of 10.0 is added and, then, an enzymatic reaction is carried out at 30° C. for 10 minutes. After the completion of the reaction, 2 ml of 0.1 M trichloroacetic acid containing 0.2 M acetic acid—0.2 M sodium acetate is added to the reaction mixture to terminate the reaction. The mixture is allowed to stand for 10 minutes or more at 30° C. and, then, is filtered through filter paper. Five milliliter of 0.4 M sodium carbonate and 1 ml of five times diluted "phenol reagent" are added to 1 ml of the filtrate obtained above and the mixture is allowed to stand at 30° C. for 20 minutes to develop color. Thereafter, the absorbency of the colored mixture is measured at 660 nm. The unit of enzyme is determined according to "Commission on Biochemical Nomenclature" (Comprehensive Biochemistry Vol 13, P26–27, 1973), in which the amount of alkaline protease which liberates trichloroacetic acid-soluble substances exhibiting the color development at 660 nm corresponding to 1 mol of tyrosine from 1% casein substrate having a pH of 10.0 at 30° C. for 1 second is defined as "1 katal".

The physicochemical properties of the alkaline protease API-21 (referred to as the present enzyme hereinbelow) will now be described in detail.

(1) Activity

Hydrolyzes proteins such as casein, hemoglobin, albumin, globulin, meat protein, fish protein, and soybean protein.

(2) Effect of pH on Enzymatic Activity

Figure 1:
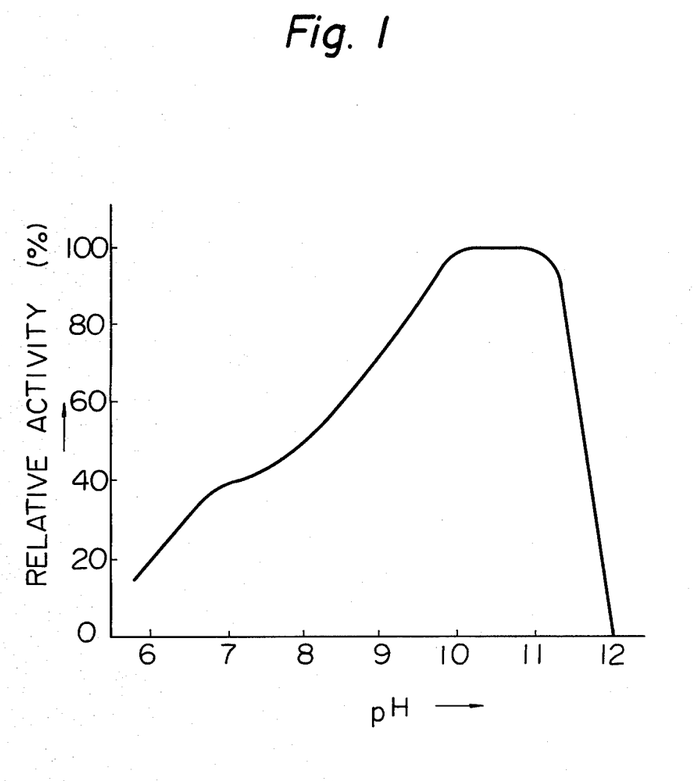
FIG. 1 graphically illustrates the optimum pH range of the enzyme according to the present invention.

As shown in FIG. 1, optimum pH is about 10 to about 11. The relative activity was determined as follows.

Each buffer solution (0.5 ml) listed below containing 2% milk casein was added to 50 $\mu l$ of the present enzyme solution to prepare a test solution.

| pH | Buffer solution |
|---|---|
| 6–9 | 0.1 M potassium phosphate - 0.05 M sodium borate |
| 9–11 | 0.1 M sodium carbonate - 0.1 M boric acid - potassium chloride |
| 11–12 | 0.1 M disodium hydrogenphosphate - sodium hydroxide |

The enzymatic activity of the test solution was determined in the manner as described above. The relative activity (%) was calculated, in which the enzymatic activity at a pH of 10.0 was defined as 100%.

(3) Effect of pH on Stability without Substrate

Figure 2:
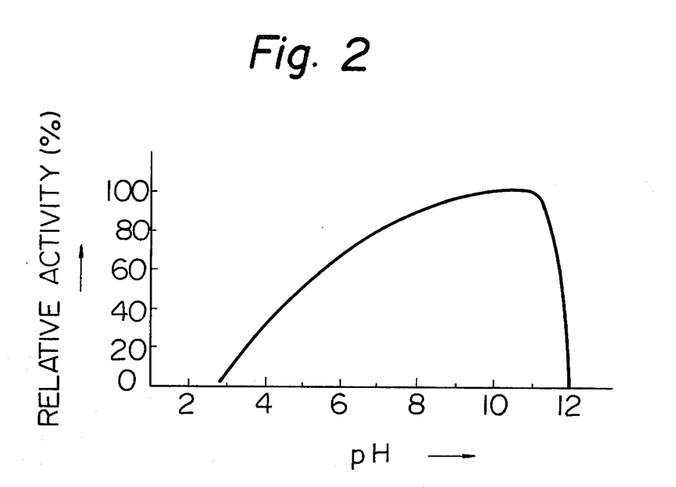
FIG. 2 graphically illustrates the stability, against pH, of the enzyme without substrate according to the present invention.

As shown in FIG. 2, the present enzyme is stable in the range of pH of about 7 to about 11.5.

The stability of the present enzyme was evaluated as follows.

Each buffer solution (0.5 ml) listed below was added to 50 μl of the present enzyme solution dialyzed and adequately diluted and the mixture was incubated at 30° C. for 10 minutes.

| pH | Buffer solution |
|---|---|
| 3–8 | 0.1 M citric acid - 0.2 M disodium hydrogenphosphate |
| 8–11 | 0.1 M sodium carbonate - 0.1 M boric acid - potassium chloride |
| 11–12 | 0.15 M disodium hydrogen phosphate - sodium hydroxide |

After incubating 9.5 ml of a 0.1 M carbonate buffer solution containing 2% casein and having a pH of 10.0 was added to the mixture. The enzymatic activity of the mixture was determined in the manner as described above. The relative activity (%) was calculated, in which the enzymatic activity at a pH of 10.0 was defined as 100%.

As shown in FIG. 2, the present enzyme was most stable at a pH of about 10 to about 11. In this pH region, the original activity of the present enzyme was completely retained. Furthermore, 80% or more of the remaining activity was exhibited at a pH of 7 to 11.5.

Figure 3:
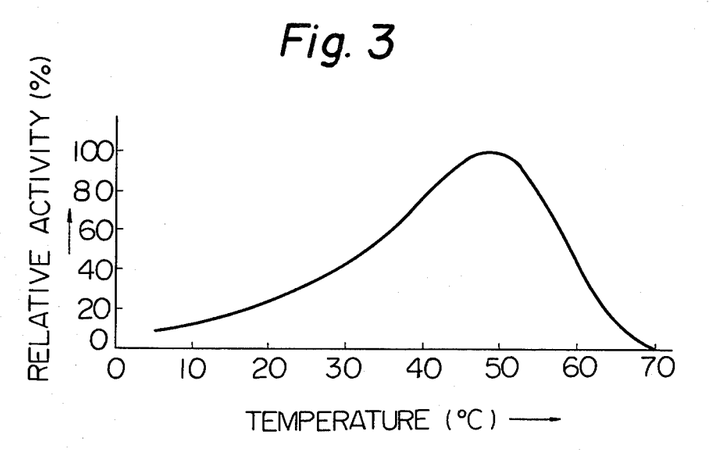
FIG. 3 graphically illustrates the active temperature range and the optimum temperature of the enzyme according to the present invention.

(4) Effect of Temperature on Enzymatic Activity As shown in FIG. 3, the present enzyme was active against casein at a temperature of 5° to 65° C. and at a pH of 10.0. The optimum temperature was 45° to 50° C.

(5) Effect of Temperature on Stability without Substrate

Figure 4A:
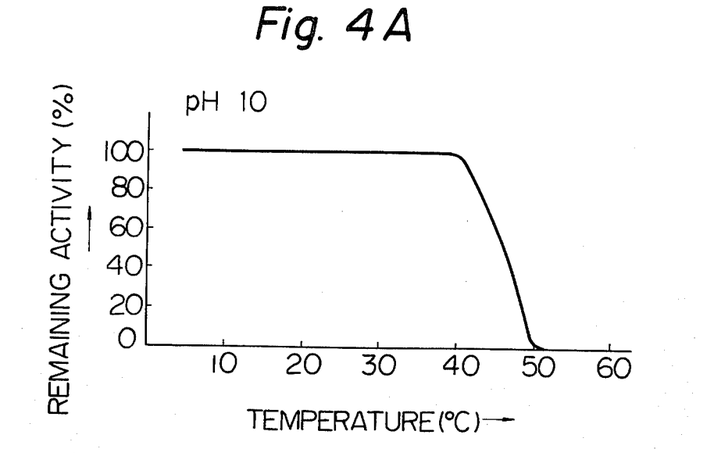
FIGS. 4A and 4B graphically illustrate the stabilities, against temperatures, of the enzyme without substrate according to the present invention at pH's of 10 and 8, respectively.
Figure 4B:
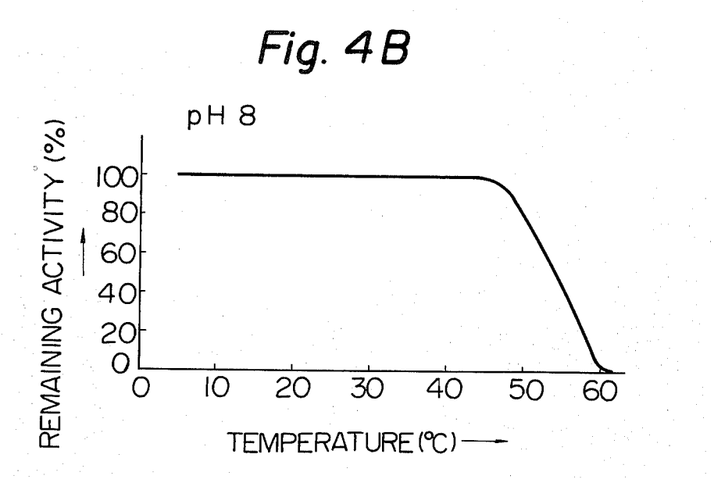

As shown in FIGS. 4A and 4B, the activity of the present enzyme is completely retained up to 40° C. upon heating without substrate at a pH of 10.0 for 10 minutes, but most of the activity was lost at 50° C. Furthermore, the activity of the present enzyme is retained up to 45° C. at a pH of 8 for 10 minutes, but the deactivation occurred at 50° C. and the enzyme was substantially deactivated at 60° C.

(6) Stability on Storing

The present enzyme is stable against freezing and freeze-drying. No substantial decrease in the activity of the freeze-dried sample was observed when the sample was allowed to stand at room temperature for 2 weeks. When the freeze-dried sample was stored in a desiccator at a room temperature, the activity of the present enzyme was completely retained.

(7) Inhibition

The present enxyme was remarkably inhibited by an active serine residue inhibitor such as diisopropyl-fluorophosphoric acid (DFP) and phenylmethanesulfonyl fluoride (PMSF). It was also inhibited by benzyloxycarbonyl-phenyl-alanine-chloromethyl ketone (ZPCK). However, the present enzyme was not inhibited by tosyl-phenylalanine-chloromethyl ketone (TPCK), which is an inhibitor of an animal serine protease, chymotrypsin, and tosyl-lysine-chloromethyl ketone (TLCK), which is a trypsin inhibitor.

Furthermore, the activity of the present enzyme was not adversely affected by the addition of p-chloro-mercury benzoate (PCMB) and ethylenediaminetetraacetate (EDTA). In addition, the activity of the present enzyme was not adversely affected by the addition of pepstatin. As a result of the above-mentioned inhibition tests, it is clear that the present enzyme is a protease having a serine residue in the active site.

(8) Determination Method of Enzymatic Activity
As mentioned above.

(9) Molecular Weight
The molecular weight of the present enzyme is about 22000 as estimated by a gel filtration over Sephadex (Trademark) G-75 at a pH of 10.

(10) Isoelectric Point
The isoelectric point of the present enzyme is 7.4 as estimated by an electrofocusing method.

(11) Ultraviolet (UV) Absorption
The absorption peak is present at 275 to 282 μm in a UV absorption spectrum.

(12) Infrared (IR) Absorption Spectrum
As shown in FIG. 5.

(13) Elemental Analysis
Omitted by the reason that the characteristic differences in these kind of high molecular weight substances such as the present enzyme can not be well manifested by the comparison of the contents of elements thereof such as carbon, nitrogen or hydrogen.

(14) Amino Acid Composition
Amino acid composition of API-21 calculated tentatively on the basis of the results by acid hydrolysis of the enzyme except for cysteine/cystine and tryptophan, while by performic acid decomposition for cysteine/cystine analysis and by alkaline decomposition for tryptophan analysis, according to the method described in the literature ("Methods in Enzymology" volume XI, 1967. Academic Press, New York.) were shown in Table 1, with the compositions of other alkaline proteases, whose data were cited from the literature[*1, *2].

As shown in Table 1, there are great differences between API-21 and other enzymes cited in amino acid compositions such as serine, arginine, lysine, valine, alanine, tryptophan, proline, and so on.

TABLE 1

Comparison of Amino Acid Compositions between API-21 and Other Alkaline Proteases

| Amino Acid | API-21 | subtilisin Novo[*1] | subtilisin Carlsberg[*2] |
|---|---|---|---|
| Lysine | 4 | 11 | 9 |
| Histidine | 8 | 6 | 5 |
| Arginine | 8 | 2 | 4 |
| Tryptophan | 0 | 3 | 1 |
| Aspartic acid/ | 27 | 11 | 9 |
| Asparagine | | 17 | 19 |
| Threonine | 10 | 13 | 19 |
| Serine | 17 | 37 | 32 |
| Glutamic acid/ | 14 | 4 | 5 |
| Gultamic | | 11 | 7 |
| Proline | 7 | 14 | 9 |
| Glycine | 30 | 33 | 35 |
| Alanine | 26 | 37 | 41 |
| Valine | 20 | 30 | 31 |
| Methionine | 4 | 5 | 5 |
| Isoleucine | 10 | 13 | 10 |
| Leucine | 14 | 15 | 16 |
| Tyrosine | 12 | 10 | 13 |
| Phenylalanine | 4 | 3 | 4 |
| Cysteinel cystine | 0 | 0 | 0 |

[*1] J. Biol. Chem., 243,5296 (1968)
[*2] J. Biol. Chem., 243,2134 (1968)

As is clear from the above-mentioned results, the present enzyme, which has an optimum pH of 10 to 11, retains the activity at a relatively low temperature, but is deactivated at a relatively high temperature (i.e., 50° C. or more). The present enzyme having these physicochemical properties will now be compared with those of known similar alkaline proteases.

Among extracellular alkaline proteases derived from Gram positive bacteria are well-known, for example, alkaline protease (subtilisin carlsberg) derived from *Bacillus licheniformis* and alkaline protease (subtilisin Novo) derived from Bacillus subtilis.

These enzymes are proteases having a serine residue in the active site, a molecular weight of about 27000 to 30000 and an isoelectric point 9 to 11. Most of other reported extracellular alkaline proteases derived from genus Bacillus have a molecular weight of 25000 to 30000 and an isoelectric point 9 to 11. Most of the above-mentioned enzymes are not deactivated upon heating at 50° C. and pH 10 for 10 minutes. Known alkaline proteases having a lower molecular weight derived from genus Bacillus are alkaline proteases E-1 and E-2 derived from Batillus No. D-6, both having a molecular weight of 20000, the activity of which does not decrease at all upon heating at 50° C. and pH 9.0 (see Japanese Examined Patent Publication (Kokoku) No. 56-4236). Furthermore, known in the art as an alkaline protease derived from genus Bacillus are an alkaline protease derived from *Bacillus alcalophilus* NCIB 10436 and an alkaline protease derived from *Bacillus alcalophilus* NCIB 10438. These enzymes, however, retain about 90% of the activity upon heating at 50° C. and pH 10 for 10 minutes as shown in Table 2. As also shown in Table 2, alkaline proteases derived from *Bacillus licheniformis* and *Bacillus subtilis* retain 70 to 80% of the activity upon heating at 50° C. and pH 10 for 10 minutes. Thus, known alkaline proteases derived from bacteria belonging to genus Bacillus such as ti Bacillus subtilis are stable in a relatively high temperature region. Contrary to this, as mentioned above, the present enzyme loses most of its activity upon heating at 50° C. and pH 10 for 10 minutes, while it is stable upon heating at a temperature of up to 40° C. and pH 10 for 10 minutes. Furthermore, the deactivation of the present enzyme occures upon heating at about 50° C. and pH 8 for 10 minutes and most of its activity is lost at 60° C. under the same conditions. In view of the differences in the characteristics of temperature stability, molecular weight and isoelectric point, the present enzyme is clearly distinguished from the known alkaline proteases derived from bacteria belonging to genus Bacillus and has not been reported in publications. Accordingly, the present enzyme is determined as a novel enzyme and is designated as "alkaline protease API-21".

11 as mentioned above. Especially, the present enzyme retains its high activity even at a relatively low temperature (e.g., 20° C. to 30° C.), as compared with conventional enzymes for a detergent. Consequently, the present enzyme is a most desirable type of alkaline protease as an additive for a household detergent in such a country where clothes are washed at a room temperature as Japan. Furthermore, the present enzyme can also be effectively utilized in a waste treatment and sewage water treatment for a rapid decomposition of protein and for reuse of nitrogen resource, since the contents of proteins in domestic wastes and domestic sewage have recently increased. Still furthermore, the use of the present protease in a food industry such as food processing is advantageous, since the enzyme can be readily deactivated after utilization upon heating at a relatively low temperature, e.g., 50° to 60° C. Thus, the use of the present enzyme is effective from the standpoint of quality control of the processed food.

EXAMPLE

The present invention will be further illustrated by, but is by no means limited to, the following examples, in which all percentages are expressed on a weight basis unless otherwise specified.

EXAMPLE 1

The present novel strain NKS-21 was cultivated in a slant culture medium. The cultivated product was suspended in sterilized water and 0.5 ml of this suspension was used as an inoculant.

An enzyme producing culture medium containing 1% casein, 1% meat extract, 1% polypeptone and 1% sodium bicarbonate was adjusted to a pH of 9.5 or 7.2 by adding aqueous sodium hydroxide or hydrochloric acid thereto.

In a shaking cultivation (A) using a rotary shaker, 100 ml, 200 ml or 300 ml of the above-prepared medium having a pH of 9.5 was added to a 1 liter Erlenmeyer flask. After sterilization, 0.5 ml of the above-prepared NKS-21 suspension was inoculated into the culture medium and the cultivation was carried out at 20° C. and under a shaking condition of 200 rpm for 41, 65 or 89 hours.

On the other hand, in a reciprocal shaking cultivation (B), 100 ml of the above-prepared culture medium having a pH of 9.5 or 7.2 was added to a 500 ml Sakaguchi flask. After sterilization, 0.5 ml of the above-prepared NKS-21 suspension was inoculated into the culture

TABLE 2

| Alkaline protease | Molecular weight | Isoelectric point | Remaining activity (%) upon heating at a pH of 10 for 10 minutes | |
|---|---|---|---|---|
| | | | 50° C. | 60° C. |
| Alkaline protease derived from *Bacillus licheniformis* | 27,287[*3] | 9.4[*3] | 78 | <2 |
| Alkaline protease derived from *Bacillus subtilis* | 27,537[*4] | 9.1[*4] | 70 | <1 |
| Alkaline protease derived from *Bacillus alcalophilus* NCIB 10436 | — | — | 94 | 73 |
| Alkaline protease derived from *Bacillus alcalophilus* NCIB 10438 | 25,000 | — | 85 | 63 |
| Alkaline protease derived from *Bacillus* NKS-21 | 22,000 | 7.4 | 6 | 1 |

[*3]Fette Seiten Anstrichmettel. 75, p 49 (1973)
[*4]The Enzymes vol III p 564 (1971)

The present enzyme "API-21" can be used with a detergent builder and thus it can be useful as a detergent additive, since it is stable at a pH of 7 to 11.5 and the maximum enzymatic activity is attained at a pH of 10 to medium and the reciprocal shaking cultivation was carried out under shaking condition of 110 cpm at 30° C. for 66 or 90 hours.

After the cultivation, the cultured product was centrifuged at 28000×g for 15 minutes, and the resultant supernatant solution was recovered. The alkaline protease activity of this solution was determined in a manner as described above.

The results are shown in Tables 3 and 4.

TABLE 3

Results of Rotary Shaking Cultivation (A)
(20° C., Initial pH of medium = 9.5)

| Amount of medium (ml) | Enzymatic activity (microkatal/liter) | | |
|---|---|---|---|
|  | 41 hr | 65 hr | 89 hr |
| 100 | 1.3 | 2.6 | 2.7 |
| 200 | 2.0 | 4.3 | 4.0 |
| 300 | 2.5 | 5.6 | 5.4 |

TABLE 4

Results of Reciprocal Shaking
Cultivation (B) (30° C.)

| Initial pH of medium | Enzymatic activity (microkatal/liter) | |
|---|---|---|
|  | 66 hr | 90 hr |
| 9.6 | 4.5 | 3.0 |
| 7.2 | 4.9 | 3.4 |

When NKS-21 was subjected to a reciprocal shaking cultivation at 30° C., the growth of NKS-21 was good not only at an initial medium pH of 9.5 but also at an initial medium pH of 7.2 and the desired alkaline protease API-21 was produced at a high rate in each case. As in the case of an initial medium pH of 9.5, the similar results were obtained when NKS-21 was cultivated in a reciprocal shaker at 20° C. and at an initial medium pH of 7.2.

Seven liters of the supernatant solution after the centrifugal separation of the NKS-21 cultured product obtained above was cooled to 3° C. Then, two times by volume of ethyl alcohol previously cooled to 3° C. was added to the cooled supernatant solution to form precipitates. The resultant precipitates were centrifugally separated in a cooled centrifugal separator at 11000×g and, then, the separated precipitates were immediately freeze dried in vacuo. Thus, 15.7 g of the desired enzyme powder was obtained.

The specific activity of alkaline protease thus obtained based on 1 kg of the protein was 0.71 microkatal (0.71 μkatal/kg.protein) and the recovery yield was 33%, where the protein was determined according to a Lowry method.

The freeze-dried enzyme sample thus obtained was dissolved in 0.01 M sodium carbonate-boric acid-potassium chloride buffer solution (pH 10.0) containing 0.2 M sodium chloride. The enzyme solution was gel filtrated over a column (2 cmo×74 cm) packed with Sephadex G-75 (Trademark available from Pharmacia fine Chemicals. AB, Sweden) previously equilibrated with the above-mentioned buffer solution to fractionate 3 ml each of eluates. The purified enzyme was obtained from main fractions which had high enzymatic activity. The enzyme thus obtained had a molecular weight of about 22,000 as estimated by a gel filtration over Sephadex G-75 (Trademark) at a pH of 10 and an isoelectric point of 7.4 as estimated by an electrofocusing method. The specific activity of the enzyme thus obtained increased by about 10 times as compared with that without gel filtration and obtained the specific activity based on 1 kg of protein was 7.0 microkatal. The recovery yield was 70%.

EXAMPLE 2

The production of alkaline protease in a 500 liter fermentation tank and the subsequent production of the enzyme preparation were carried out by using alkaline protease producing strain NKS-21.

An enzyme producing culture medium containing 1% casein, 1% meat extract, 1% polypeptone and 1% sodium bicarbonate was adjusted to a pH of 9.5 by adding aqueous sodium hydroxide thereto. A 300 ml amount of the above-prepared medium was added to a 1 liter Erlenmeyer flask. After sterilization, 0.5 ml of the NKS-21 suspension prepared in the same manner as mentioned in Example 1 was inoculated into the culture medium and the cultivation was carried out at 20° C. for 3 days. 300 ml of the resultant cultured product was added to a sterilized 30 l jar-fermentor containing 10 l of the above-prepared culture medium having a pH of 9.5. Then, aerobic agitating cultivation was carried out at 20° C. for 3 days under the conditions of an agitation speed of 400 rpm and an aeration rate of 12 l/min.

After cultivation in the 30 l jar-fermentor for 3 days, 10 l of the cultured product was transferred to a sterilized 500 l fermentation tank containing 220 l of the above-prepared culture medium having a pH of 9.5. Then, an aerobic agitating cultivation was carried out at 20° C. for 4 days under the conditions of an agitation speed of 400 rpm and an aeration rate of 200 l/min.

After the cultivation, the cultured product was centrifuged at 11000×g in a cooled continuous centrifugal separator, and 200 l of the supernatant solution was obtained. This supernatant solution was cooled to 3° C. Then, twice the volume of ethyl alcohol previously cooled to 3° C. was added to the cooled supernatant solution to precipitate the desired alkaline protease. The precipitated alkaline protease API-21 was centrifugally separated at about 11000×g in a cooled continuous centrifugal separator and, then, the separated alkaline protease API-21 was immediately freeze dried in vacuo. Thus, the following freeze-dried alkaline protease API-21 enzyme preparation was obtained.

| Recovered enzyme weight (g) | 1230 |
|---|---|
| Specific activity (microkatal/kg protein) | 0.52 |
| Recovery yield (%) | 70 |

The enzyme thus obtained was purified in the same manner as mentioned in Example 1 to obtain alkaline protease having a molecular weight of about 22000 and an isoelectric point at a pH of 7.4.

We claim:

1. Alkaline protease API-21 having the following physicochemical properties:
   (1) Activity: Hydrolyzes casein under alkaline conditions, with an optimum pH range of 10 to 11, and has optimum temperature range for activity of 45° C. to 50° C.;
   (2) Stability: No decrease in enzymatic activity observed up to 40° C. upon heating without temperature substrate for 10 minutes at a pH of 10, but a 90% or more decrease of enzymatic activity observed at 50° C. for 10 minutes at a pH of 10. Deactivation occurs at 50° C. upon heating for 10 minutes at a pH of 8 and complete deactivation substantially occurs at 60° C. for 10 minutes at a pH of 8. The protease is stable under alkaline conditions, especially within a pH range of 7 to 11.5, and is stable against freezing and freeze-drying; and (3) Enzyme molecule: The protease is protein having a molecular weight of about 22000 as estimated by a gel filtration method, an isoelectric point of 7.4 as estimated by an electrofocusing method, an absorption peak of 275 to 282 nm in a UV absorption spectrum, IR absorption characteristics as shown in FIG. 5, and a serine residue in the active site thereof.

2. A method for preparing alkaline protease API-21 comprising the steps of:
(a) cultivating species of NKS-21 of genus Bacillus capable of producing alkaline protease API-21 in an alkaline culture medium; and
(b) recovering alkaline protease API-21 from the cultivated product.

* * * * *